United States Patent
Choi et al.

(10) Patent No.: US 7,294,492 B2
(45) Date of Patent: Nov. 13, 2007

(54) PROCESS FOR THE MANUFACTURE OF SPIROKETALS

(75) Inventors: Kwang-Pil Choi, Morganville, NJ (US); Michael P. McLean, Mattawan, NJ (US); John Lyons Buckley, III, Middletown, NJ (US); Mark L. Dewis, Matawan, NJ (US)

(73) Assignee: International Flavors & Fragrances Inc.

( * ) Notice: Subject to any disclaimer, the term of this patent is extended or adjusted under 35 U.S.C. 154(b) by 384 days.

(21) Appl. No.: 11/031,720

(22) Filed: Jan. 7, 2005

(65) Prior Publication Data

US 2006/0154347 A1     Jul. 13, 2006

(51) Int. Cl.
*C12P 15/00*     (2006.01)
(52) U.S. Cl. ...................................... 435/127
(58) Field of Classification Search ................. 435/127
See application file for complete search history.

(56) References Cited

U.S. PATENT DOCUMENTS

| | | | |
|---|---|---|---|
| 3,144,465 A | 8/1964 | Ruzicka et al. | |
| 4,798,799 A | 1/1989 | Farbood et al. | |
| 4,970,163 A | 11/1990 | Farbood et al. | |
| 5,212,078 A | 5/1993 | Farbood et al. | |
| 5,440,050 A | 8/1995 | do Ceu Goncalves da Costa et al. | |

OTHER PUBLICATIONS

*The Biotransformation of the Diterpenoid, Sclareol, by Cephalosporium Aphidicola*, James R. Hanson et al., Phytochemistry, vol. 36, No. 4, pp. 903-906, (1994).

*Key to the species of the Hyphozyma (yeast-like 52 Hyphomycetes) and description of H. roseonigra sp. nov.*, G.S. De Hoog and M. Th. Smith, Antonie van Leeuwenhoek, pp. 39-44, (1986).

*Chemical-Microbiological Semisynthesis of enantio-Ambrox Derivatives*, Andres Garcia-Granados et al., Tetrahedron 55, pp. 8567-8578, (1999).

*Labdane and Kaurane Diterpenoids from Plectranthus fruticosus*, Christina Gaspar-Marques et al., Journal Natural Products, vol. 66, pp. 491-496, (2003).

*Microbial Matabolism of the Diterpene Sclareol: Oxidation of the A Ring by Septomyxa affinis*, Samir A. Kouzi and James D. McChesney, Helvetica Chimica Acta, vol. 73, pp. 2157-2164, (1990).

*The Production of Crystalline Manool from Dacrydium Biforme*, D.F. Merz and W.J. Ritchie, N.Z. Jl. Sci. vol. 13, pp. 268-286, (1970).

*Metabolism, Macromolecular Synthesis, and Nuclear Behavior of Cryptococcus albidus at 37 C*, S.L. Tang and D.H. Howard, Journal of Bacteriology, vol. 115, No. 2, pp. 574-581, Aug. 1973.

*Bensingtonia Ciliata Gen.et. sp.nov., a Ballistosporic Fungus*, C.T. Ingold, Trans. Br. Mycol. Soc. 86(2), pp. 325-328, (1986).

*Hydroxylation and Glucoside Conjugation in the Microbial Metabolism of the Diterpene Sclareol*, Samir A. Kouzi and J.D. McChesney, Xenobiotica, vol. 21, No. 10, pp. 1311-1323, (1991).

*Microbial Models of Mammalian Metabolism: Fungal Metabolism of the Diterpene Sclareol by Cunninghamella Species*, Samir A. Kouzi and J.D. McChesney, Journal Natural Products, vol. 54, No. 2, pp. 483-490, Mar.-Apr. 1991.

*Primary Examiner*—Leon B. Lankford, Jr.
*Assistant Examiner*—Susan Hanley
(74) *Attorney, Agent, or Firm*—Elizabeth M. Quiel; Joseph F. Leightner

(57) ABSTRACT

The present invention is directed to the use of yeasts to produce spiroketal fragrance materials. The preferred yeasts used in the method of the invention are *Bensingtonia ciliate* and *Cryptococcus laurentii*.

8 Claims, No Drawings

PROCESS FOR THE MANUFACTURE OF SPIROKETALS

FIELD OF THE INVENTION

The invention relates to a novel route to the manufacture of spiroketal products, more specifically to Amber Ketal, through the use of a bioprocess.

BACKGROUND OF THE INVENTION

Spiroketals are known in the art and are commercially useful as fragrance materials. The industrial processes for the production of these compounds generally start form sclareol and manool and yield mixtures of the oxygenated spiroketals of formula

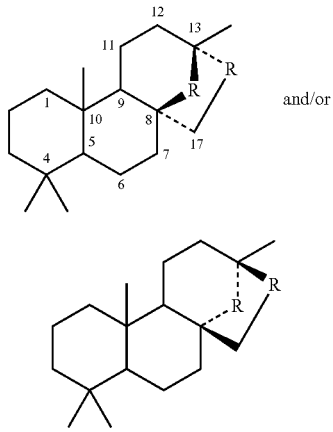

For example, U.S. Pat. No. 3,144,465 discusses the synthesis of a mixture of the oxygenated spiroketals I and II (R═O) starting from manool, by the epoxidation with peracetic, perbenzonic, monoperphthalic, percamphoric or performic acid, followed by oxidation. A further process also described [E. Demole, Experientia, 20, 609 (1964)] the semi-industrial production of a mixture of the oxygenated spiroketals I and II (R═O) starting from manool, which combines the epoxidation by perbenzoic acid with the ozonolysis of the resulting epoxide, the products thus obtained being then treated with p-toluenesulphonic acid. These methods lead to mixtures of the spiroketals I and II (R═O) in yields not higher than 30% and have the disadvantage of using toxic and/or expensive reagents, as well as the added disadvantage of producing mixtures of compounds in which one of the components is odorless, thereby reducing the commercial value of the final product for the application in the industry of perfumery.

As discussed in U.S. Pat. Nos. 4,970,163 and 5,212,078; U.S. Pat. No. 4,798,799 discloses the utilization of a culture containing the microorganism Hyphozyma roseoniger ATCC 20624 capable of producing the diol having the structure:

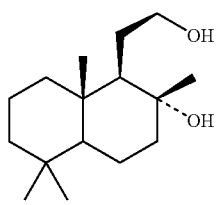

in a recoverable quantity upon the transformation of compounds including the sclareol compound having the structure:

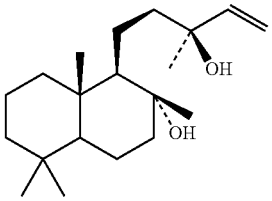

Table 4, Col. 12 of this patent discloses yields of 96% when carrying out the reaction:

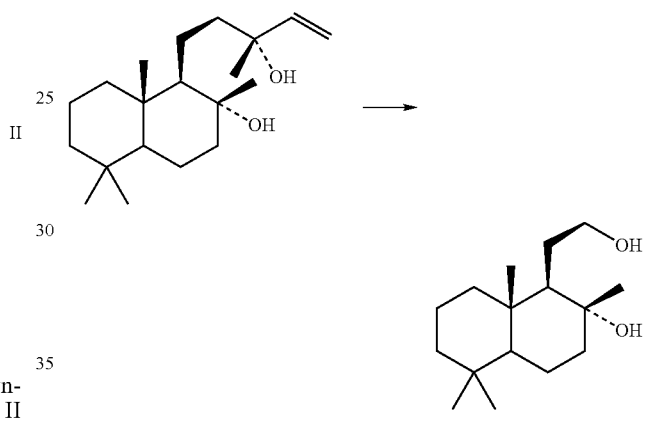

under fermentation conditions using ATCC 20624.

U.S. Pat. Nos. 4,970,163 and 5,212,078 disclose carrying out the reaction

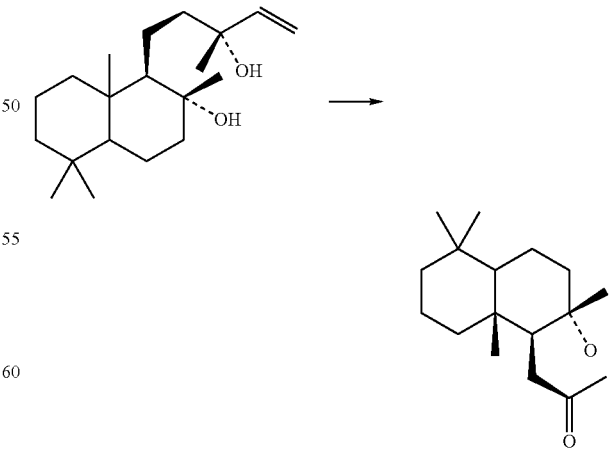

via microbiological methods using the organism *Bensingtonia ciliata*, ATCC 20919 and carrying out the reaction

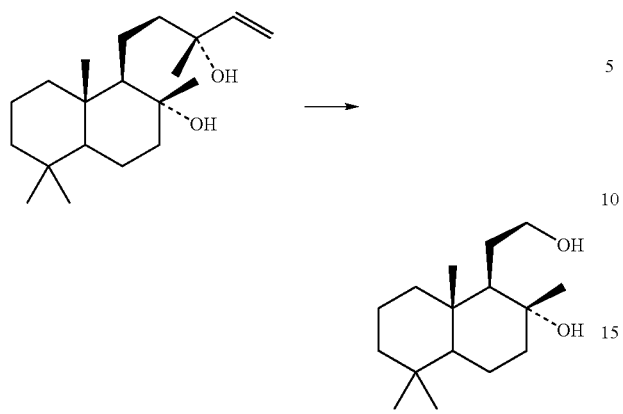

via microbiological methods using the organism *Cryptococcus laurentii*, ATCC 20920.

Since manool, manool ketone and larixol ketone are valuable intermediates in production of the important compounds in perfumery, such as amber ketal, there is an ongoing need for the methods of carrying out these reactions to be developed.

SUMMARY OF THE INVENTION

One embodiment of the invention provides a method for preparing manool from larixol via the microbiological process using yeast. In a particularly preferred embodiment the yeast is the organism *Bensingtonia ciliata*, ATCC 20919.

Another embodiment of the invention provides a method for preparing manool ketone from manool via the microbiological process using yeast. In a particularly preferred embodiment the yeast is the organism *Cryptococcus laurentii*, ATCC 20920.

The invention also provides a method for preparing manool ketone from larixol via the microbiological process using yeast, with the preferred embodiment being the organisms *Bensingtonia ciliata*, ATCC 20919 and *Cryptococcus laurentii*, ATCC 20920.

These and other embodiments of the present invention will be apparent by reading the following specification and claims.

DETAILED DESCRIPTION OF THE INVENTION

As was described in the Background of the Invention, the present invention is directed to the discovery that yeast can be used to produce the fragrance materials set forth in this application. Yeasts have been previously employed to manufacture diol and lactone compounds. There was no suggestion that these yeasts could be used to produce the spiroketals of the present invention.

More, specifically, there is no teaching or suggestion in the prior art of either carrying out the reaction of

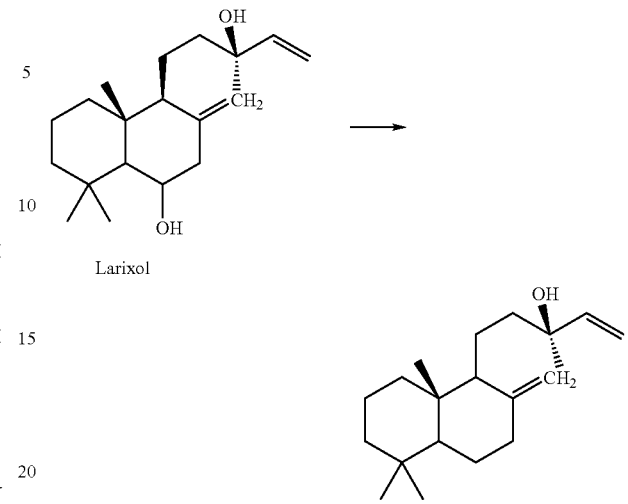

Larixol

Manool via microbiological methods using a yeast such as the organism *Bensingtonia ciliata*, ATCC 20919 or carrying out the reaction

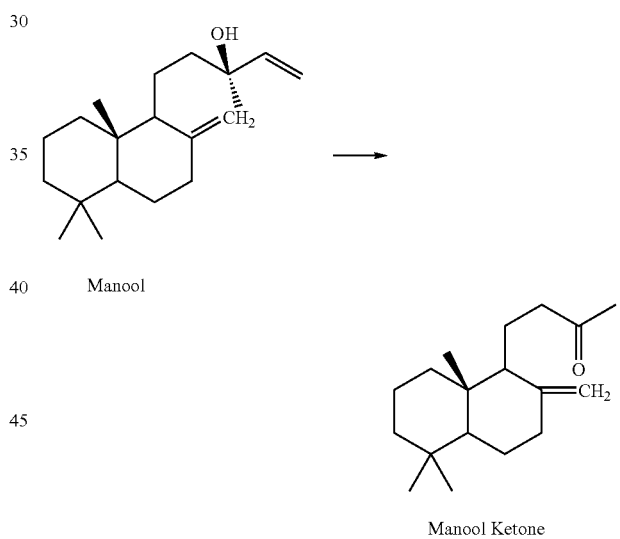

Manool

Manool Ketone via microbiological methods using yeast such as the organism *Cryptococcus laurentii*, ATCC 20920.

or carrying out the reaction

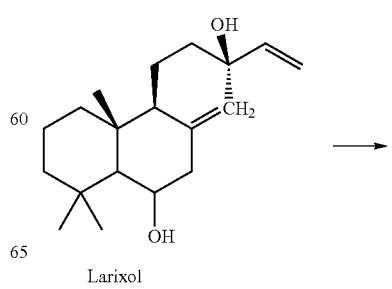

Larixol

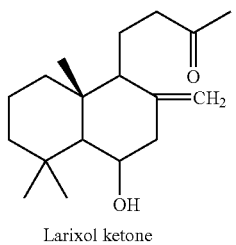

Larixol ketone via microbiological methods using yeast such as the organism *Cryptococcus laurentii*, ATCC 20920.

The yeasts of the present invention are available from the American Type Culture Collection (ATCC) from Manassas, Va. USA. The yeasts are commercially available from ATCC by use of its webpage, atcc.org. Both yeasts, *Bensingtonia ciliate* and *Cryptococcus laurenti* are previously on deposit with ATCC from earlier work performed by the assignee of the present application, International Flavors & Fragrances Inc., New York, N.Y. 10019.

The yeasts of the present invention can be incorporated in any appropriate media such as agar, with the accompanying nutrients such as sugars and lipids, growth factors and the like. In the following examples media was prepared using $NH_4NO_3$, $KH_2PO_4$, $MgSO_4 \cdot 7H_2O$ and yeast extract. As noted in the following examples, Pluronic L92, available from BASF for the purpose of dispersed substrates. Obviously the key factor is that the components are compatible with yeasts and do not negatively impact the yeasts.

The starting materials of the present invention, larixol and manool are commercially available fragrance materials and are available from International Flavors & Fragrances Inc.

The present invention is conducted by contacting the yeasts with the starting materials for a period of from about 72 hours to about 240 hours, preferably from about 110 hours to about 200 hours and most preferably from about 144 hours to about 168 hours. The temperature that the yeasts is provided ranges from about 12° C. to about 33° C., more preferably at about 25° C. Preferably, the yeasts and the starting materials are contacted by mild agitation.

The present invention provide the desired products in yields, Manool from Larixol is greater than 15%, preferably greater then 25%, most preferably greater then 40% by weight. The desired yield of Manool ketone from Manool is greater than 87%, preferably greater then 90%, most preferably greater then 92% by weight. The desired yield of Larixol ketone from Larixol is greater than 72%, preferably greater then 80%, most preferably greater then 85% by weight. After the products are obtained the desired products are separated from the other reactant materials by conventional processes such as filtration, distillation and other techniques known in the art.

The following examples are provided as specific embodiments of the present invention. Other modifications of this invention will be readily apparent to those skilled in the art, without departing from the scope of this invention. As used herein all percentages are weight percent unless noted to the contrary.

EXAMPLES

Example 1

Conversion of Larixol Using *Bensingtonia ciliata* ATCC 20919, *Cryptococcus laurentii* ATCC 20920, *Cryptococcus albidus* saito, skinner var. *albidus* ATCC 20918, *Cryptococcus albidus* ATCC 20921.

The following medium was prepared:

| | |
|---|---|
| $NH_4NO_3$ | 0.1% |
| $KH_2PO_4$ | 0.1% |
| $MgSO_4 \cdot 7H_2O$ | 0.05% |
| Yeast Extract | 0.2% |

4 Flasks were prepared. Each 500 ml flask contained 100 ml medium and 1 gram of Manool (98%) in Pluronic L92® (2:1).

Each flask was inoculated with 5 ml of a 48 hour grown cell culture in dextrose at 25° C., and 150 revolutions per minute (rpm). Product and substrate was monitored by gas chromatography (GC) against known standards.

In the following table the following codes are used:
S: Substrate
P: Product
I: Intermediate
TI: Trace Intermediate.

The "substrate" is Larixol having the structure:

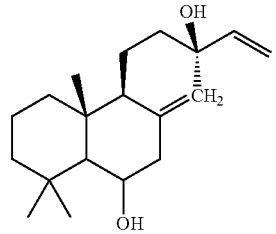

The "product" is Manool having the structure:

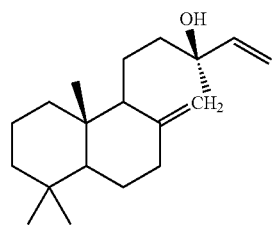

The "intermediate" is Larixol ketone having the structure:

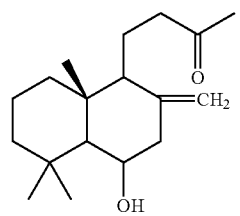

The "trace intermediate" is Manool ketone having the structure:

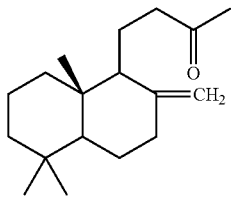

TABLE I

| Strains | Duration 24 Hours | Duration 48 Hours | Duration 72 Hours |
| --- | --- | --- | --- |
| *Bensingtonia ciliata* | S | S + P | S + P + TI |
| *Cryptococcus laurentii* | S | S + I | S + I |
| *Cryptococcus albidus* saito, skinner var. *albidus* | S | S | S + P + I + TI |
| *Cryptococcus albidus* | S | S | S + P + I + TI |

Example 2

Preparation of Manool from Larixol using *Bensingtonia ciliata* ATCC 20919 Reactions:

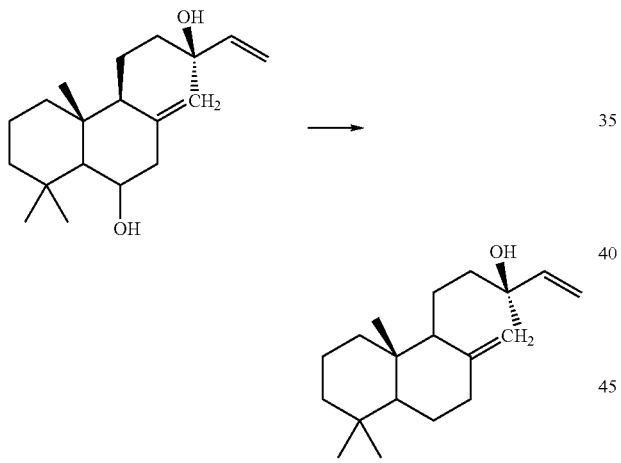

The following medium was prepared:

| | |
| --- | --- |
| $NH_4NO_3$ | 0.1% |
| $KH_2PO_4$ | 0.1% |
| $MgSO_4 \cdot 7H_2O$ | 0.05% |
| Yeast Extract | 0.2% |
| Dextrose | 1% |

Into a 500 ml flask was placed 100 ml medium and a 1:1 mixture of Larixol powder: Pluronic L92®. 1 gram of the Manool and 1 gram of Pluronic L92® mixture was added to the flask and inoculated with 5 ml of isolate of *Bensingtonia ciliata* ATCC 20919. After one week at 25° C. and 150 rpm, the resulting product was extracted with 300 ml volumes of ethyl acetate and then dried over anhydrous sodium sulfate. The solvent was removed on a rotary evaporator. The residue was dissolved in ethyl acetate. The resulting extract permitted to evaporate for a period of 24 hours where upon crystal (150 mg) of Manool was recovered.

Example 3

Conversion of Manool Using *Bensingtonia ciliata* ATCC 20919, *Cryptococcus laurentii* ATCC 20920, *Cryptococcus albidus* saito, skinner var. *albidus* ATCC 20918, *Cryptococcus albidus* ATCC 20921.

The following medium was prepared:

| | |
| --- | --- |
| $NH_4NO_3$ | 0.1% |
| $KH_2PO_4$ | 0.1% |
| $MgSO_4 \cdot 7H_2O$ | 0.05% |
| Yeast Extract | 0.2% |

Four flasks were prepared. Each 500 ml flask contained 100 ml medium and 1 gram of Manool (98%) in Pluronic L92® (2:1).

Each flask was inoculated with 5 ml of a 48 hour grown cell culture in dextrose at 25° C., and 150 revolutions per minute (rpm). Product and substrate was monitored by gas chromatography (GC) against known standards.

In the following table the following codes are used:
S: Substrate
P: Product
I: Intermediate
TI: Trace Intermediate.

The "substrate" is Manool having the structure:

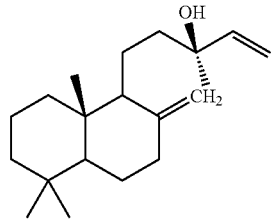

The "product" is Manool Ketone having the structure:

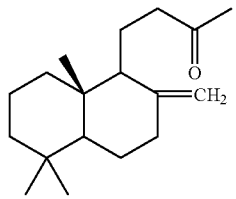

The "intermediate" is Manool Alcohol having the structure:

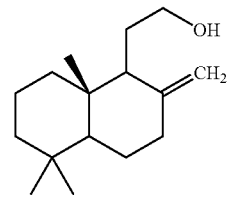

The "trace intermediate" is Manool Aldehyde having the structure:

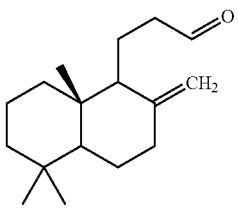

TABLE I

| Strains | Duration 24 Hours | Duration 48 Hours | Duration 72 Hours |
| --- | --- | --- | --- |
| Cryptococcus laurentii | S + P | S + P | S + P + I |
| Bensingtonia ciliata | S | S + P | S + P + I |
| Cryptococcus albidus saito, skinner var. albidus | S | S + P + I | S + P + I + TI |
| Cryptococcus albidus | S | S + P + I | S + P + I + TI |

Example 4

Preparation of Manool Ketone from Manool using *Cryptococcus laurentii* ATCC 20920 Reactions:

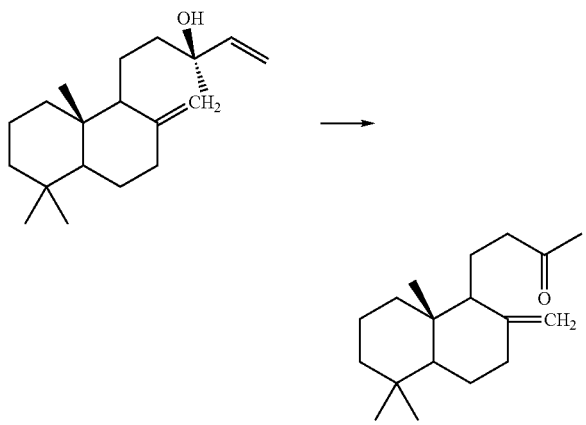

The following medium was prepared:

| | |
| --- | --- |
| $NH_4NO_3$ | 0.1% |
| $KH_2PO_4$ | 0.1% |
| $MgSO_4 \cdot 7H_2O$ | 0.05% |
| Yeast Extract | 0.2% |
| Dextrose | 1% |

Into a 500 ml flask was placed 100 ml medium and a 1:1 mixture of Manool powder: Pluronic L92®. 1 Gram of the Manool and 1 gram of Pluronic L92® mixture was added to the flask and inoculated with 5 ml of isolate of *Cryptococcus laurentii* ATCC 20920. After one week at 25° C. and 150 rpm, the resulting product was extracted with 300 ml volumes of ethyl acetate and then dried over anhydrous sodium sulfate. The solvent was removed on a rotary evaporator. The residue was dissolved in ethyl acetate. The resulting extract is permitted to evaporate for a period of 24 hours where upon liquid (approximately 350 mg) of Manool Ketone was recovered.

Example 5

Preparation of Manool Ketone from Manool using *Cryptococcus laurentii* ATCC 20920
Reactions:

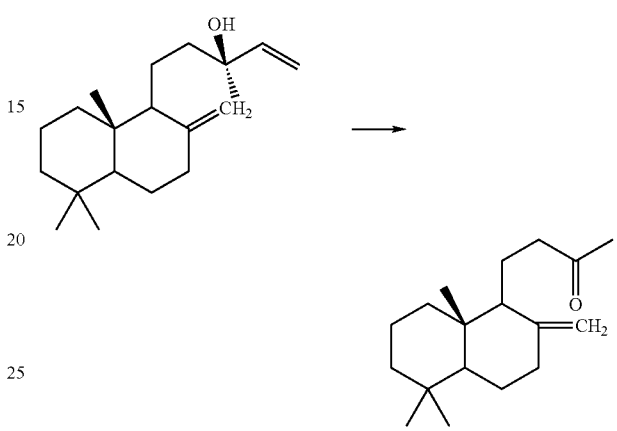

In each of the following examples, mixtures of Manool and Pluronic L92® were prepared to form a Manool paste and added with 50% glucose. A fermentation broth was prepared containing the indicated amounts of:
$NH_4NO_3$
$KH_2PO_4$
$MgSO_4 \cdot 7H_2O$
Yeast Extract
Antifoam Material ("AF")
Water.

The Manool emulsion and 50% glucose solution was added to the fermentation shake flask containing the fermentation medium and the cultures, *Cryptococcus laurentii* ATCC 20920. At the end of the given period of time liquid Manool Ketone was recovered.

Example 5(A)

| | |
| --- | --- |
| Manool | 120 g |
| Pluronic L92 ® | 60 g |
| 50% glucose | 240 g |
| | 420 g    0.286 g Manool/g emulsion. |

315 g Emulsion - 90 g Manool

| Broth | | Parameters |
| --- | --- | --- |
| 20.0 g | $NH_4NO_3$ | 25° C. |
| 10.0 g | $KH_2PO_4$ | 0.15 vvm |
| 5.0 g | $MgSO_4 \cdot 7H_2O$ | 400 rpm |
| 20.0 g | Yeast Extract | |
| 10.0 g | AF | |
| 8.5 | Liter De-ionized $H_2O$ | |

Inoculation:
1 Fresh shake flask (500 ml/48 hr)
Add 315 g emulsion of Manool 315 of emulsion were added over the course of the fermentation up to a total of 420 g emulsion or 120 g Manool (12 g/L).

Recovery: 10.5 g/L Manool Ketone in 7 days.

NMR of Manool Ketone

NMR. Both $^{1}$H and $^{13}$C NMR experiments were performed on a Bruker Avance 500-MHz spectrometer. CDCl$_3$ containing TMS was used as solvent.

Manool Ketone: $^{1}$H NMR (CDCl$_3$, 500 MHz) δ 0.69 (s, 3H), 0.80 (s, 3H), 0.87 (s, 3H), 1.07-1.10 (m, 2H), 1.18-1.21 (m, 1H), 1.31-1.40 (m, 2H), 1.50-1.58 (m, 4H), 1.71-1.73 (m, 1H), 1.78-1.86 (m, 2H), 1.95-1.98 (m, 1H), 2.09 (s, 3H), 2.30-2.38 (m, 2H), 2.56-259 (m, 1H), 4.44 (s, 1H), 4.82 (s, 1H); $^{13}$C NMR (CDCl$_3$, 500 MHz) δ 14.1 (CH$_3$), 17.3 (CH$_2$), 19.2 (CH$_2$), 21.5 (CH$_3$), 24.3 (CH$_2$), 29.8 (CH$_3$), 33.36 (C), 33.44 (CH$_3$), 38.1 (CH$_2$), 38.8 (CH$_2$), 39.6 (C), 42. 0, (CH$_2$), 42.7 (CH$_2$), 55.3 (CH), 56.1 (CH), 106.2 (CH$_2$), 148.0 (C), 208.9 (C).

Manool: $^{1}$H NMR (CDCl$_3$, 500 MHz) δ 0.67 (s, 3H), 0.80 (s, 3H), 0.87 (s, 3H), 1.02 (d, J=13.0 Hz, oft, J=3.9 Hz, 1H), 1.07 (d, J=12.6 Hz, of d, J=2.7 Hz, 1H), 1.17 (d, J=13.4 Hz, of t, J=4.0 Hz, 1H), 1.27 (s, 3H), 1.29-1.40 (m, 4H), 1.44-1.49 (m, 1H), 1.50-1.61 (m, 4H), 1.67-1.74 (m, 2H), 1.76-1.79 (m, 1H), 1.96 (d, J=12.9 Hz, oft, J=5.0 Hz, 1H), 2.35-2.39 (m, 1H), 4.48 (s, 1H), 4.80 (s, 1H), 5.05 (d, J=10.8 Hz, of d, J=1.2 Hz, 1H), 5.20 (d, J=17.4 Hz, of d, J=1.19 Hz, 1H), 5.91 (d, J=17.3 Hz, of d, J=10.8 Hz, 1H); $^{13}$C NMR (CDCl$_3$, 500 MHz) δ 14.4 (CH$_3$), 17.6 (CH$_2$), 19.4 (CH$_2$), 21.7 (CH$_3$), 24.4 (CH$_2$), 28.0 (CH$_3$), 33.55 (C), 33.6 (CH$_3$), 38.4 (CH$_2$), 39.1 (CH$_2$), 39.8 (C), 41.4 (CH$_2$), 42.2 (CH$_2$), 55.6 (CH), 57.2 (CH), 73.6 (C), 106.3 (CH$_2$), 111.6 (CH$_2$), 145.1 (CH), 148.7 (C).

Example 5(B)

Fermenter #1 10 L (Inoculation for Fermenter #2)
Organism: *Cryptococcus laurentii* ATCC 20920 (from freeze glycerol stock)
Manool Ketone producer.

Broth:

| | | |
|---|---|---|
| 20.0 g | NH$_4$NO$_3$ | At time of inoculation |
| 20.0 g | Yeast Extract | 100 g Glucose added as 50% |
| 10.0 g | KH$_2$PO$_4$ | solution (sterilized separately) |
| 10.0 g | AF | |
| to 9.5 | Liter H$_2$O | |

Parameters:

25° C.
0.15 vvm
400 rpm

Inoculation:

Glycerol stock - 500 ml shake flask, 1% glucose, followed by 500 ml Shake flask - fermenter in 48 hours.

The culture was grown for 24 hrs. then used as inoculation for fermenter #2.

Fermenter #2: 100 L
Organism: *Cryptococcus laurentii* ATCC 20920 (from freeze glycerol stock)

Broth:

| | |
|---|---|
| 200.0 g | NH$_4$NO$_3$ |
| 200.0 g | Yeast Extract |
| 100.0 g | KH$_2$PO$_4$ |
| 50.0 g | MgSO$_4$.7H$_2$O |
| 200.0 g | Manool |
| 100.0 g | Pluronic L92 ® |
| 100.0 g | AF |
| to 90.2 | Liter w/H$_2$O |

Parameters:

25° C.
0.15 vvm
300 rpm

Time:

| | |
|---|---|
| 0 hours | Inoculation 500 ml |
| | pH 6.08 |
| | DO = 100% |
| | Add 200 g of Manool, 100 g of Pluronic L92, 200 g of Dextrose |
| About 21 hours | pH 6.16 |
| | DO = 92% |
| About 29 hours | pH 6.6 |
| | DO = 87% |
| | Add 400 g of Manool, 400 g of Pluronic L92, 400 g of Dextrose |
| About 45 hours | pH 3.48 |
| | DO = 92% |
| About 69 hours | pH 6.0 |
| | DO = 94% |
| About 77 hours | pH 6.26 |
| | DO = 89% |
| | Add 400 g of Manool, 400 g of Pluronic L92, 400 g of Dextrose |
| About 124 hours | pH 5.16 |
| | DO = 93% |
| About 127 hours | pH 5.3 |
| | DO = 91% |
| | Add 200 g of Manool, 200 g of Pluronic L92 |
| About 141 hours | pH 5.54 |
| | DO = 95% |
| About 165 hours | pH 5.91 |
| | DO = 96% |
| | Terminate fermentation by sterilization 121° C., 30 min |

Recovery; 10.1 g/L of Manool Ketone in 7 days

Example 6

Preparation of Larixol Ketone from Larixol using *Cryptococcus laurentii* ATCC 20920

Reactions:

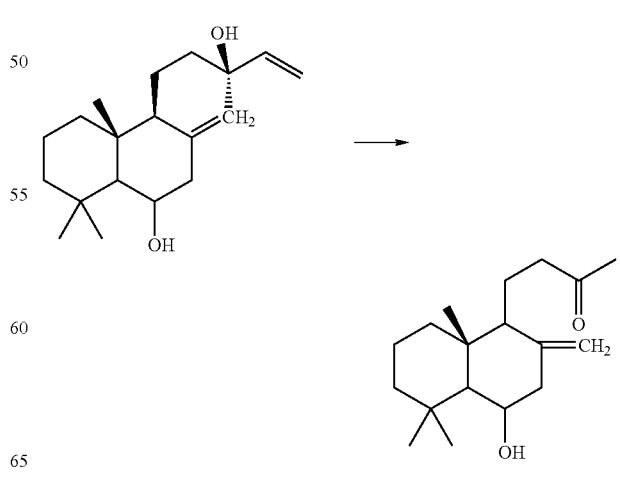

The following medium was prepared:

| | | |
|---|---|---|
| $NH_4NO_3$ | 0.1% | |
| $KH_2PO_4$ | 0.1% | |
| $MgSO_4 \cdot 7H_2O$ | 0.05% | |
| Yeast Extract | 0.2% | |
| Dextrose | 1% | |

Into a 500 ml flask was placed 100 ml medium and a 1:1 mixture of Larixol powder: Pluronic L92®. 1 Gram of the Larixol and 1 gram of Pluronic L92® mixture was added to the flask and inoculated with 5 ml of isolate of *Cryptococcus laurentii* ATCC 20920. After one week at 25° C. and 150 rpm, the resulting product was extracted with 300 ml volumes of ethyl acetate and then dried over anhydrous sodium sulfate. The solvent was removed on a rotary evaporator. The residue was dissolved in ethyl acetate. The resulting extract is permitted to evaporate for a period of 24 hours where upon pure crystals (550 mg) of Larixol ketone. were recovered.

Example 7

Preparation of Larixol Ketone from Larixol using *Cryptococcus laurentii* ATCC 20920

Reactions:

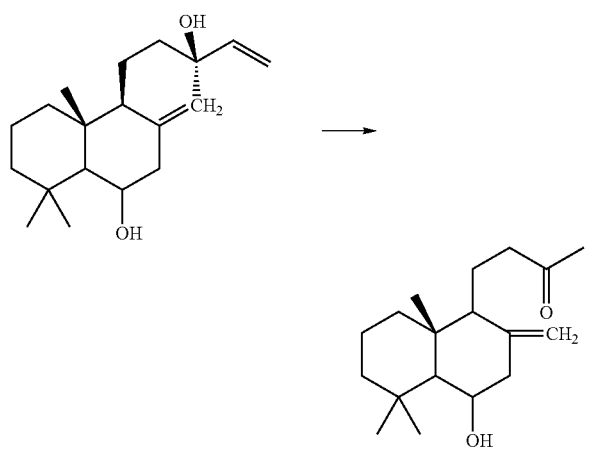

| | | |
|---|---|---|
| Larixol | 120 g | |
| Pluronic L92 ® | 120 g | |
| Glycerol | 120 g | |
| | 360 g | 0.33 g Larixol/g emulsion. |

| 273 g Emulsion - 90 g Larixol | | |
|---|---|---|
| Broth | | Parameters |
| 20.0 g | $NH_4NO_3$ | 25° C. |
| 10.0 g | $KH_2PO_4$ | 0.15 vvm |
| 5.0 g | $MgSO_4 \cdot 7H_2O$ | 400 rpm |
| 20.0 g | Yeast Extract | |
| 10.0 g | AF | |
| 8.5 | Liter De-ionized $H_2O$ | |

Inoculation:
1 Fresh shake flask (500 ml/48 hr)
Add 273 g emulsion of Larixol
273 g of emulsion was added over the course of the fermentation up to a total of 364 g emulsion or 120 g Larixol (12 g/L).

Product Recovery:
Products were recovered by sieving, dissolving in Ethyl acetate and recrystallizing with heating and cooling.
Final Recovery: 8.6 g/L Manool Ketone in 7 days.

NMR of Larixol Ketone
$^1$H NMR (CDCl$_3$, 500 MHz) δ 0.71 (s, 3H), 1.01 (s, 3H), 1.07-1.15 (m, 3H), 1.16 (s, 3H), 1.35-1.39 (m, 1H), 1.45-1.57 (m, 3H), 1.59-1.61 (m, 1H), 1.74-1.77 (m, 1H), 1.85-1.91 (m, 1H), 2.00-2.05 (t, J=11.4 Hz, 1H), 2.11 (s, 3H), 2.30-2.37 (m, 1H), 2.56-2.62 (m, 1H), 2.6 (d, J=12.2 Hz, of d, J=4.87 Hz, 1H), 3.38-3.67 (m, 1H), 3.83 (d, J=10.7 Hz, of t, J=4.9 Hz, 1H), 4.51 (d, J=1.3 Hz, 1H), 4.90 (d, J=1.3 Hz, 1H); $^{13}$C NMR (CDCl$_3$, 500 MHz) δ 15.9 (CH$_3$), 17.7 (CH$_2$), 19.1 (CH$_2$), 22.3 (CH$_3$), 30.0 (CH$_3$), 33.9 (C), 36.6 (CH$_3$), 39.2 (CH$_2$), 39.4 (C), 42.8 (CH$_2$), 43.7 (CH$_2$), 49.0 (CH$_2$), 55.4 (CH), 60.4 (CH), 71.6 (CH), 108.2 (CH$_2$), 145.3 (C), 209.1(C).

NMR of Larixol
$^1$H NMR (CDCl$_3$, 500 MHz) δ 0.69 (s, 3H), 1.01 (s, 3H), 1.02-1.04 (m, 1H), 1.10 (d, J=10.6 Hz, 1H), 1.17 (s, 3H), 1.20-1.32 (m, 3H), 1.27 (s, 3H), 1.34-1.38 (m, 2H), 1.45-1.50 (m, 2H), 1.53-1.58 (m, 3H), 1.71-1.76 (m, 2H), 2.04 (t, J=11.2 Hz, 1H), 2.67 (d, J=12.1 Hz, of d, J=4.8 Hz, 1H), 3.83 (m, 1H), 4.60 (s, 1H), 4.89 (s, 1H), 5.05 (d, J=10.8 Hz, 1H), 5.20 (d, J=17.4 Hz, 1H), 5.91 (d, J=17.3 Hz, of d, J=10.8 Hz, 1H); $^{13}$C NMR (CDCl$_3$, 500 MHz) δ 16.0 (CH$_3$), 18.0 (CH$_2$), 19.1 (CH$_2$), 22.3 (CH$_3$), 27.7 (CH$_3$), 33.9 (C), 36.6 (CH$_3$), 39.3 (CH$_2$), 39.6 (C), 41.4 (CH$_2$), 43.7 (CH$_2$), 49.2 (CH$_2$), 56.5 (CH), 60.5 (CH), 71.6 (CH), 73.5 (C), 108.4 (CH$_2$), 111.6 (CH$_2$), 145.2 (CH), 145.6 (C).

We claim:

1. A method for preparing manool comprising contacting larixol with a yeast selected from the group consisting of *Bensingtonia ciliata* ATCC 20919, *Cryptococcus albidus* saito, skinner var. *albidus* ATCC 20918, and *Cryptococcus albidus* ATCC 20921 in a fermentation medium to produce said manool.

2. A method for preparing manool ketone comprising contacting manool with a yeast selected from the group consisting of *Bensingtonia ciliata* ATCC 20919, *Cryptococcus laurenti*, ATCC 20920, *Cryptococcus albidus* saito, skinner var. *albidus* ATCC 20918, and *Cryptococcus albidus* ATCC 20921 in a fermentation medium to produce said manool ketone.

3. A method for preparing larixol ketone comprising contacting larixol with a yeast selected from the group consisting of *Cryptococcus laurentii* ATCC 20920. *Cryptococcus albidus* saito, skinner var. *albidus* ATCC 20918, and *Cryptococcus albidus* ATCC 20921 in a fermentation medium to produce said larixol ketone.

4. The method of claim 1, wherein the conversion of larixol to manool is at least 15% based upon the concentration of larixol.

5. The method of claim 2, wherein the conversion of manool to manool ketone is at least 87% based upon the concentration of manool.

6. The method of claim 3, wherein the conversion of larixol to larixol ketone is at least 72% based upon the concentration of larixol.

7. A method for preparing manool ketone comprising a two step process whereby the first step employs contacting a first yeast with larixol in a fermentation medium to form a first reaction product, and the second step employs contacting a second yeast with the first reaction product in a fermentation medium to form manool ketone, wherein the first yeast is selected from the group consisting of *Bensingtonia ciliata* ATCC 20919, *Cryptococcus albidus* saito, skinner var. *albidus* ATCC 20918, and *Cryptococcus albidus* ATCC 20921, and the second yeast is selected from the group consisting of *Bensingtonia ciliata* ATCC 20919, *Cryptococcus laurentii* ATCC 20920, *Cryptococcus albidus* saito, skinner var. *albidus* ATCC 20918, and *Cryptococcus* albidus ATCC 20921.

8. The method of claim 7, wherein the first yeast is *Bensingtonia ciliata* ATCC 20919 and the second yeast is *Cryptococcus laurentii* ATCC 20920.

* * * * *